United States Patent
Nelson et al.

(10) Patent No.: US 10,497,471 B1
(45) Date of Patent: Dec. 3, 2019

(54) SYSTEM, METHOD AND COMPUTER READABLE MEDIUM FOR USE IN PROVIDING PATIENT TREATMENT REGIME

(75) Inventors: Cindy Rae Nelson, Spanish Fort, AL (US); Craig A. Webster, Omaha, NE (US); John Lawrence Snapp, Westminster, CO (US); Rodney J. Kempkes, Omaha, NE (US)

(73) Assignee: WEST CORPORATION, Omaha, NE (US)

( * ) Notice: Subject to any disclaimer, the term of this patent is extended or adjusted under 35 U.S.C. 154(b) by 712 days.

(21) Appl. No.: 12/391,848

(22) Filed: Feb. 24, 2009

(51) Int. Cl.
- *G16H 20/10* (2018.01)
- *G16H 80/00* (2018.01)
- *G16H 10/60* (2018.01)

(52) U.S. Cl.
CPC ............. *G16H 20/10* (2018.01); *G16H 10/60* (2018.01); *G16H 80/00* (2018.01)

(58) Field of Classification Search
CPC .............................. G06Q 50/22; G06Q 50/24
USPC .......................................................... 705/2, 3
See application file for complete search history.

(56) References Cited

U.S. PATENT DOCUMENTS

| | | | | |
|---|---|---|---|---|
| 2002/0191035 A1* | 12/2002 | Selent | ........................... | 345/866 |
| 2003/0060688 A1* | 3/2003 | Ciarniello et al. | ............ | 600/300 |
| 2003/0167190 A1* | 9/2003 | Rincavage | ............ | G06F 19/328 705/3 |
| 2004/0034288 A1* | 2/2004 | Hennessy et al. | ............. | 600/300 |
| 2004/0117205 A1* | 6/2004 | Reardan et al. | ................... | 705/2 |
| 2004/0143594 A1* | 7/2004 | Kalies | .................... | G06F 19/363 |
| 2005/0069103 A1* | 3/2005 | DiVenuta et al. | ......... | 379/88.18 |
| 2005/0131737 A1* | 6/2005 | Joseph et al. | ...................... | 705/2 |
| 2005/0209885 A1* | 9/2005 | Lamb et al. | ...................... | 705/2 |
| 2006/0143060 A1* | 6/2006 | Conry | .................... | G06Q 10/06 705/7.19 |
| 2006/0253301 A1* | 11/2006 | Simms | ................ | G06F 19/3418 705/2 |
| 2007/0226010 A1* | 9/2007 | Larsen | .............................. | 705/2 |
| 2007/0282634 A1* | 12/2007 | Johnson | ................. | G16H 50/70 705/3 |
| 2008/0162352 A1* | 7/2008 | Gizewski | ......................... | 705/50 |
| 2008/0258922 A1* | 10/2008 | Kaukonen | ........... | G06F 19/3481 340/573.1 |

OTHER PUBLICATIONS

Samarth et al., Using Health Information Technology to Determine Medication Adherence, Nov. 2009, AHRQ, Publication No. 10-0010-EF, pp. 1-30 (Year: 2009).*

* cited by examiner

*Primary Examiner* — Devin C Hein

(57) ABSTRACT

A management network allows monitoring and/or automation of a patient treatment regime prescribed by a medical practice. The management network provides links between a practice management system of the medical practice and related information sources such as pharmaceutical suppliers and referred practices. A query executed on the management network determines whether the requirements of a parameter of a patient treatment regime, such as the taking of prescribed medication, are being met and generates alarm notifications where necessary to the patient and/or prescribing practitioner.

12 Claims, 6 Drawing Sheets

SYSTEM, METHOD AND COMPUTER READABLE MEDIUM FOR USE IN PROVIDING PATIENT TREATMENT REGIME

FIELD OF THE INVENTION

This disclosure relates to a system, method and computer readable medium for use in providing a treatment regime to a patient. The disclosure has particular relevance to monitoring and automating a patient treatment regime.

BACKGROUND OF THE INVENTION

In a typical relationship between a medical practitioner and a patient, the medical practitioner may prescribe a course of treatment, which may include physical and pharmaceutical therapies. However, once prescribed, the onus falls onto the patient to follow the prescribed course of treatment and there is limited opportunity for the practitioner to monitor the patient outside of visits by the patient to the medical practitioner.

What is required is a system, method and computer readable medium capable of providing increased monitoring of a patient treatment regime.

SUMMARY OF THE INVENTION

In accordance with one embodiment of the disclosure, there is provided a method of monitoring a patient treatment regime prescribed by a medical practice, the method comprising determining at least one parameter of the patient treatment regime; determining a query dependent on said at least one parameter; executing said query on at least one data source to generate a query result; determining from said query result at least one action; and performing said at least one action.

In accordance with one embodiment of the disclosure, there is provided a method of automating a treatment regime prescribed by a first medical practitioner to a patient, the method comprising determining at least one parameter of the treatment regime; determining a supplier of the at least one parameter; and causing a supply of said at least one parameter to said patient.

In accordance with one embodiment of the disclosure, there is provided a system for use in providing a treatment regime to a patient, the system comprising at least one database storing one or more patient preferences; at least one notification system; at least one data source; at least one processor; wherein the at least one processor is configured to receive at least one parameter of a patient treatment regime; wherein the at least one processor is configured to generate at least one query dependent on said at least one parameter; wherein the at least one processor is configured to execute the query on the at least one data source to produce a query result; wherein the at least one processor is configured to determine an action dependent on said query result; wherein the system is configured to generate a notification dependent on said action; and wherein the notification system is configured to provide said notification to said patient.

In accordance with one embodiment of the disclosure, there is provided a management system for use in providing a treatment regime to a patient, the management system comprising at least one processor; a database storing one or more patient notification preferences; wherein the processor is configured to generate a notification to said patient, said notification dependent on at least one parameter of said treatment regime; and wherein the generated notification is dependent on at least one of said one or more patient notification preferences.

In accordance with one embodiment of the disclosure, there is provided a computer readable medium comprising a set of instructions executable on at least one processor, the instructions comprising determining a query dependent on said at least one parameter; executing said query on at least one data source to generate a query result; determining from said query result at least one action; and performing said at least one action.

BRIEF DESCRIPTION OF THE DRAWINGS

The invention will now be described, by way of example only, with reference to specific embodiments and to the accompanying drawings in which.

DETAILED DESCRIPTION OF THE INVENTION

In many practices, such as medical, dental, legal practices and the like, a practice management system is utilized to control patient/client information gathering, billing, scheduling of appointments and other day to day data requirements. Typically, the practice management system is isolated to a particular practice, with little interaction between separate practices. An isolated practice constrains the processing of data to the data stored within the practice management system. In a medical practice for example, a medical practitioner may prescribe a course of treatment to a patient. However, the only information available to the practitioner for monitoring the patient's treatment is derived directly from the patient, such as through follow-up consultations.

Figure 1:
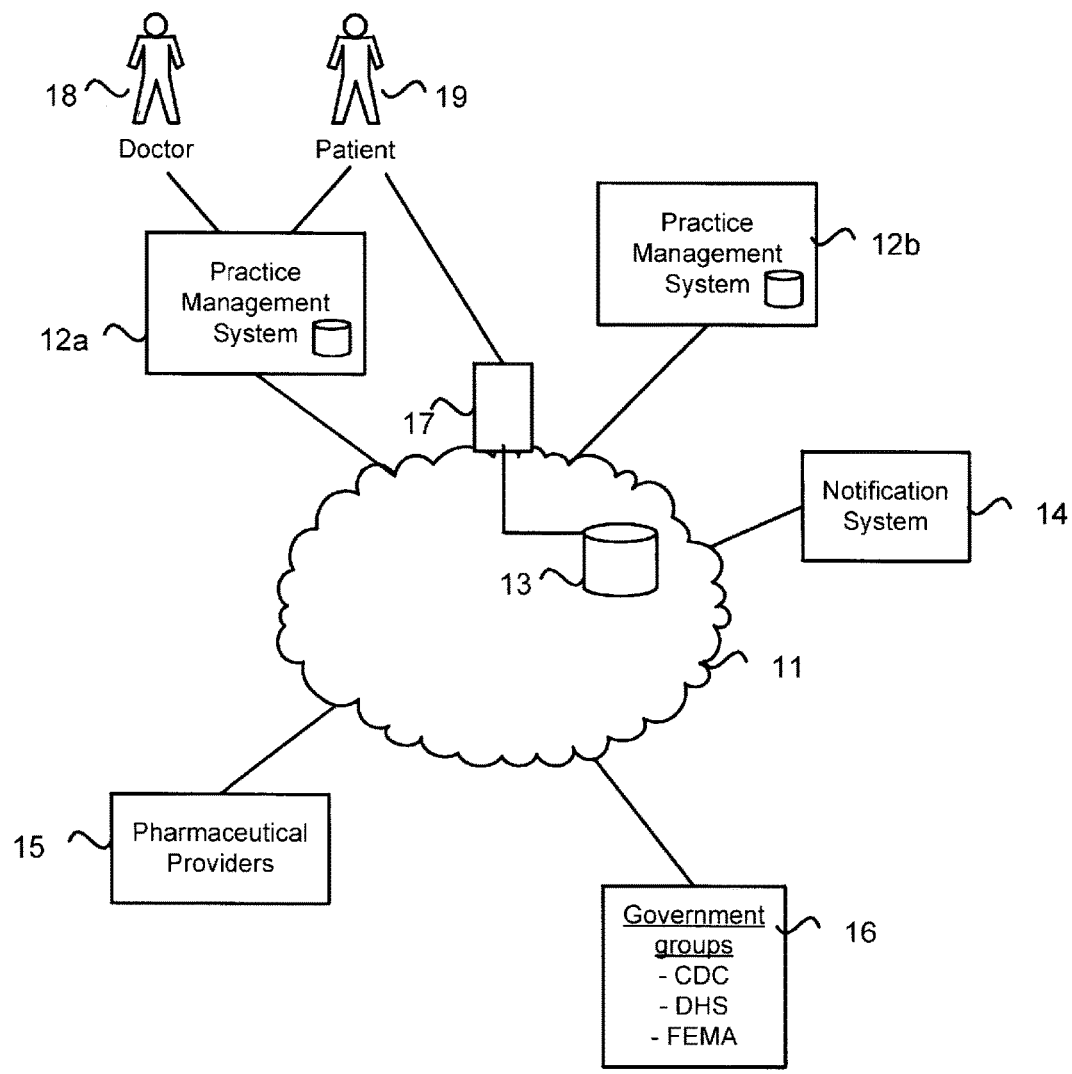
FIG. 1 schematically represents a system in accordance with an embodiment of the disclosure.

A system in accordance with an embodiment of the disclosure is shown generally at 10 in FIG. 1. In the system 10, a practice management system of a medical practice, such as system 12*a*, interfaces with a management network 11. As shown, the management network can be associated with a plurality of separate practice management systems 12*a*, 12*b*, etc. The network can provide central information storage, processing and management for the practices 12*a*, 12*b* and thus includes a database 13. The data stored in database 13 may be in addition to, or overlap with, the data stored and managed by the individual practice management systems 12*a*, 12*b* etc. In particular, the database 13 can store patient related data such as their notification preferences, medical history, current treatment regimes, etc.

The term medical practice used herein is to be considered broadly as including many different types of practices providing health related services to patients, clients or customers. A medical practice is considered to include, without limitation, the practice of a doctor, general practitioner, dentist, surgeon, specialist, physiotherapist, chiropractor, optometrist, massage therapist, nutritionist, providers of natural remedies, and all similar practices and their equivalents.

Also shown in FIG. 1 is a notification system 14. In the Applicant's co-pending application, U.S. Ser. No. 11/926,878, the entire contents of which are incorporated herein by reference, the Applicant discloses a system, method and computer readable medium for automating the process of providing notifications to recipients. The above referenced disclosure describes a notification system having application in a practice management system, such as for managing a medical practice, whereby billing and appointment reminders could be automatically generated and forwarded to patients (or responsible parties associated with the patients). A patient or responsible party is able to register notification preferences with the notification system or an associated database that controlled the delivery parameters of the notification, for example, whether the notification is delivered by phone, email, text as well as the timing of the delivery.

The management network 11 may interface with other information sources, such as pharmaceutical providers 15, referred practitioners and government bodies 16, for example, Center for Disease Control (CDC), Federal Emergency Management Agency (FEMA), regional health departments, etc. By linking to a range of information sources, there are greater opportunities for providing enhanced monitoring and patient care.

The specific form of the interfaces described herein may be embodied using any suitable communications devices known to the person skilled in the art. Communications devices may be based on wireless or wired devices and employ any suitable communications standards for data transfer and manipulation.

The system 10 is initialized by entering patient details of a patient 19 into the practice management system 12a which may include details of the prescribed treatment, details of a next appointment, billing details, personal patient details, a responsible party to be contacted on behalf of the patient, for example, a nurse, carer, parent, guardian, etc. Some or all of these details may also be uploaded from the practice management system to the database 13. Such details may be provided, for example, when the patient 19 attends the medical practice 12a for treatment.

At the time of a consultation or at some other time, which may be before or after the consultation, the patient 19 may provide other patient preferences, such as notification preferences, to the management network 11. For example, as described in the co-pending application reference above, a patient may specify a preferred message delivery type such as email, SMS, phone call etc and the requisite contact details. The patient may also specify time dependent preferences such as a work phone number or work email to be used during business hours as well as home phone number or home email to be used outside of business hours. The patient may provide their preferences to the management network 11 through an interface 17, such as a web interface direct to the management network 11. Alternatively, the patient may provide their notification preference data through a practice management system, for example, practice management system 12a.

In addition, a medical practitioner 18, such as a doctor or a nurse for example, at the medical practice 12a can register preferences, such as notification preferences, filtering preferences, treatment regime data and the like with the management network 11, for example through a web based form, or by uploading data from the practice management system to the management network 11.

Through the various above described links and associations, the management network 11 is able to access an extensive set of patient related data. These relationships can thus be brought together to provide different techniques and strategies in patient care.

Figure 2:
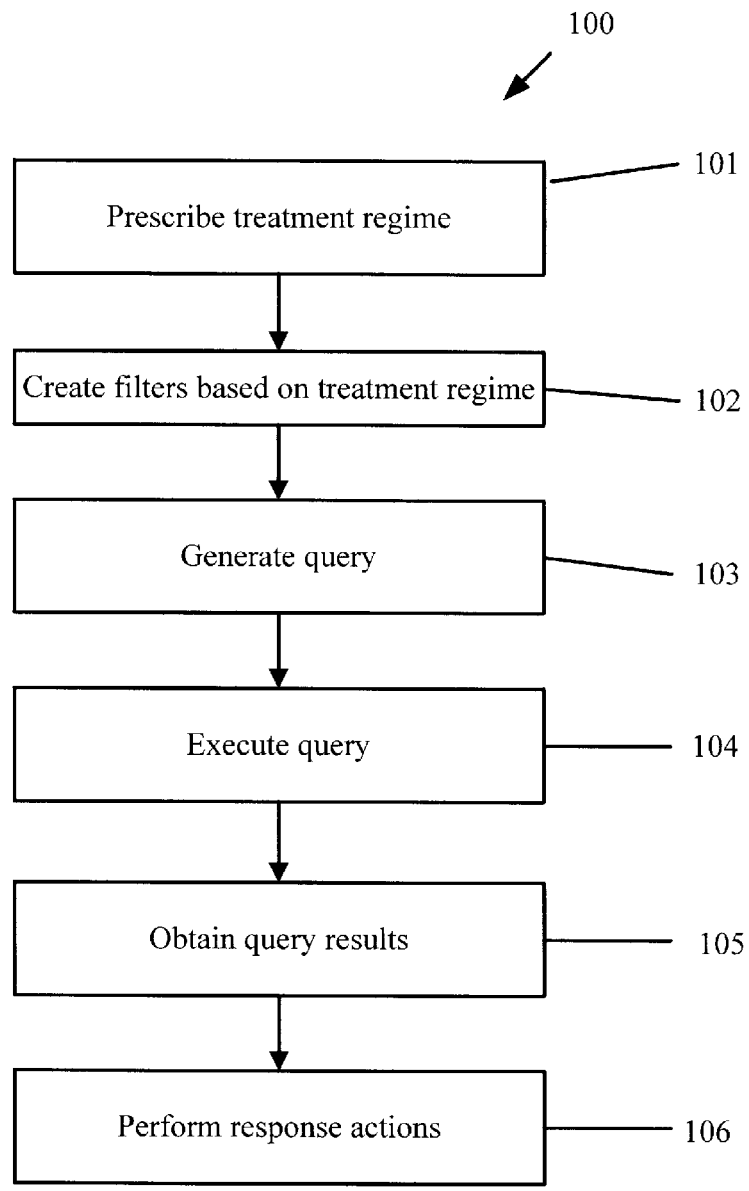
FIG. 2 shows a process flow in accordance with an embodiment of the disclosure.

Once the system 10 is initialized, a practitioner 18 is able to specify filters for monitoring and/or automating patient care. Using the filters, the management network 11 is able to search and filter data from the various sources illustrated in FIG. 1 in order to relate the data to a treatment regime of a patient. An example of the process flow 100 will be described with reference to FIG. 2. At step 101, a medical practitioner may prescribe a treatment regime to a patient. The prescribed treatment regime may include prescribed medication and pharmaceuticals, prescribed therapies, referral to other practitioners such as specialists, and any combination of these treatments as well as other treatments not specifically listed herein but which will be apparent to the person skilled in the art. When the treatment regime is prescribed, filters may be created and stored in the practice management system 12a and/or the management network 11 (step 102). The filters associate the patient with at least one parameter of the treatment regime. At step 103, the management system 11 can generate a query using the filters and execute the query (step 104) on any or all available information sources. The query results obtained at step 105 can be used to determine whether further action is necessary. Actions performed in response to query results (step 106) may include taking no further action, generating a notification to the patient or responsible party through the notification system 14, or generating a notification to the medical practitioner which may be through the notification system 14 or may be through the respective practice management system. In addition, actions may include scheduling the execution of the query more frequently, i.e. for increased monitoring of the patient, or less frequently, for reduced monitoring of the patient.

Figure 3:
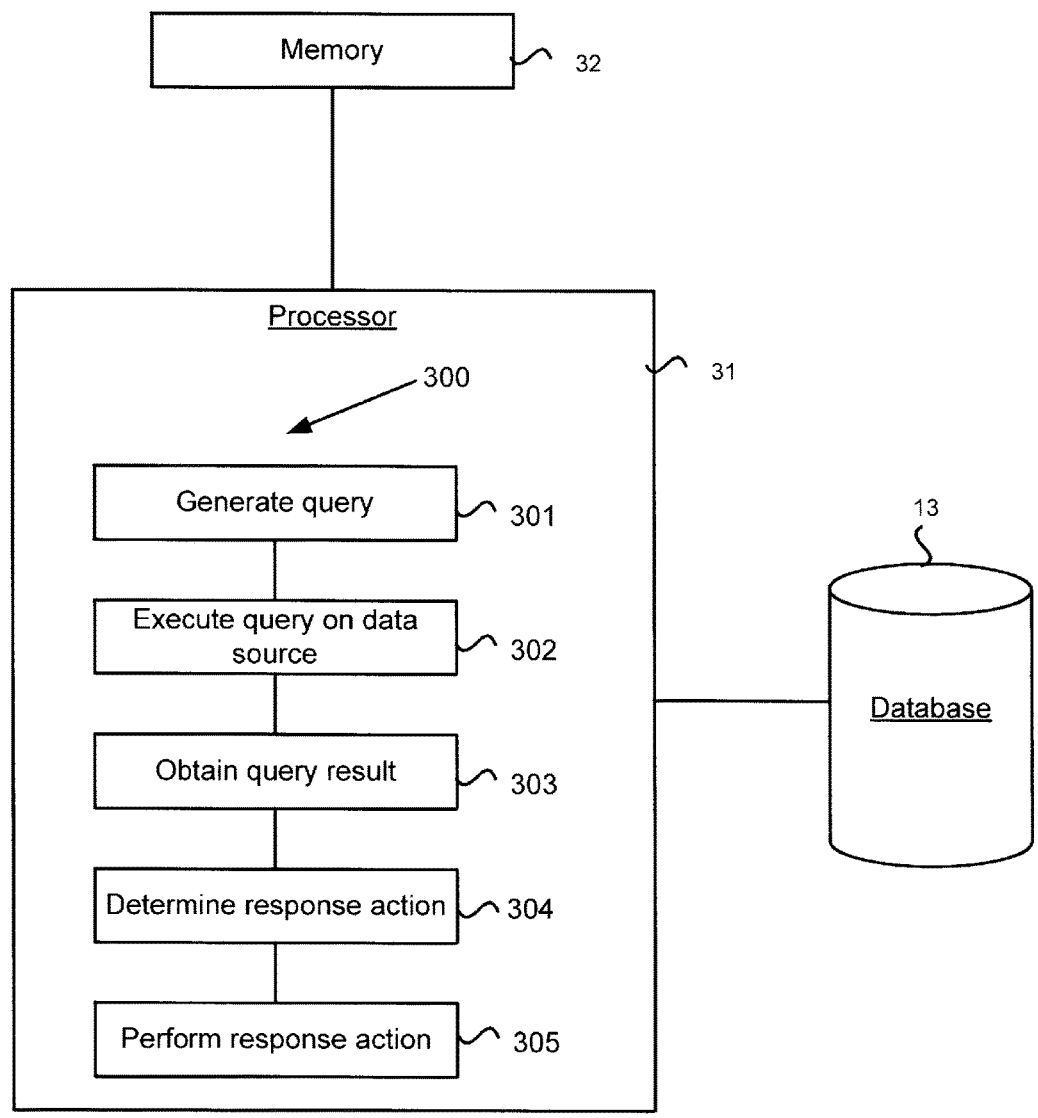
FIG. 3 shows an instruction set executed on a processor.

The management network is shown in more detail in FIG. 3 as including at least one processor 31 operatively associated with at least one memory 32 and the database 13. The memory 32 stores an instruction set 300 that can be executed on the processor 31. The instruction set causes the processor 31 to generate a query 301 and then execute the query 302 using any appropriate internal or external data source. When the query executes and produces a query result 303 the processor determines whether any response action is required 304. The processor 31 can then initiate the performing of the response action 305.

Figure 4:
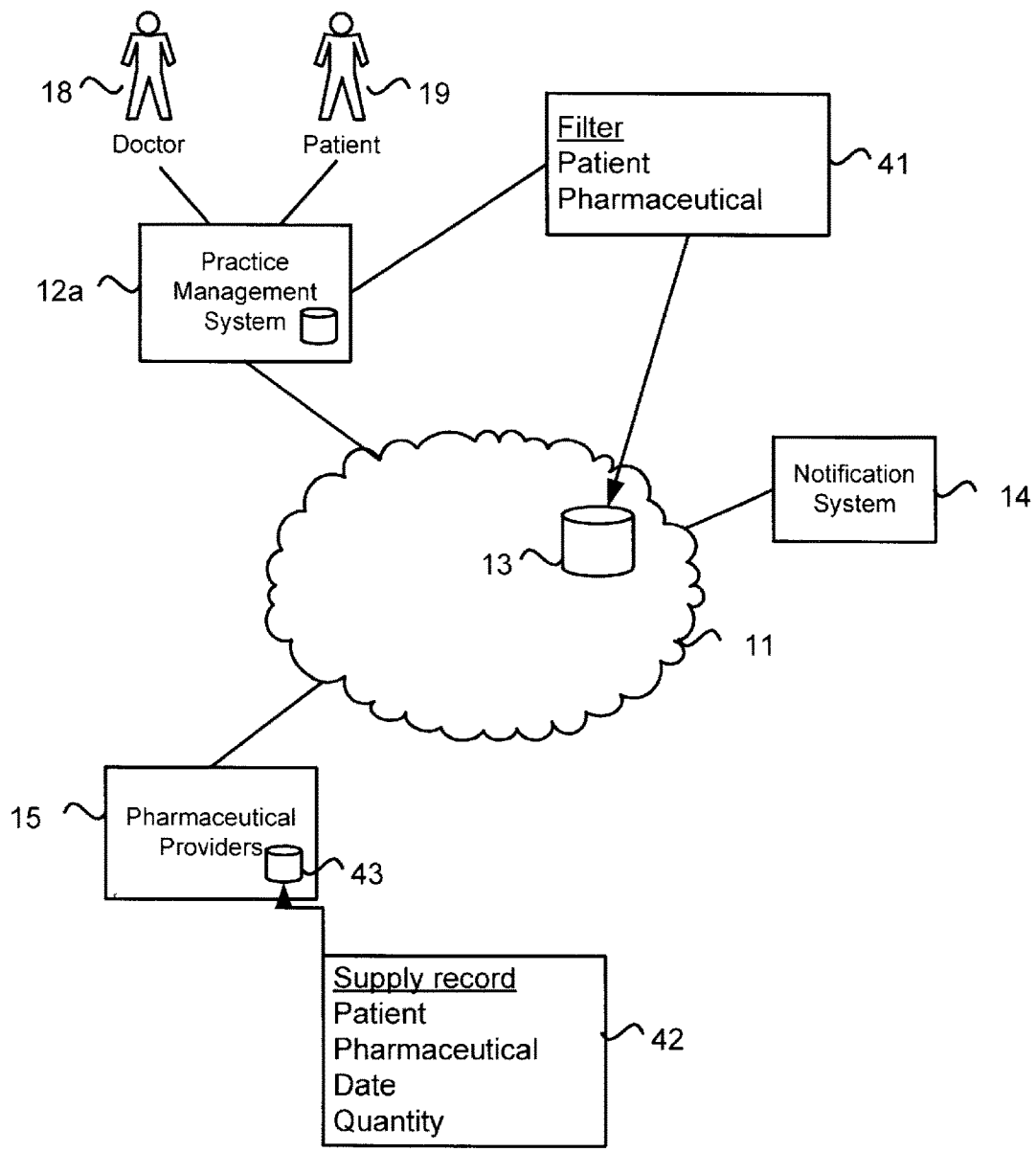
FIG. 4 schematically represents an embodiment of the disclosure relating to monitoring pharmaceuticals.

With reference to FIG. 4, in one example, a doctor 18 at a medical practice managed by practice management system 12a may prescribe a treatment regime to a patient 19 that includes a course of treatment of a particular pharmaceutical that is supplied from within the network of pharmaceutical providers 15. When the treatment regime is prescribed, a filter 41 is created in the practice management system 12a and/or the management network 11. The filter associates the patient with the pharmaceutical, being a parameter of the treatment regime.

When the patient 19 is supplied with the prescribed pharmaceutical, a record 42 is made in the data management systems 43 of the pharmaceutical network.

At some determined time, the management network executes a query on information provided by the pharmaceutical network 15. In one example, the query filters the data to determine the quantity of pharmaceutical provided to the patient over a period of time. In one embodiment, the results of the query are provided to the practice management system for further review. In one embodiment, the filter may specify acceptable limits for consumption and hence re-ordering of the pharmaceutical. If the query results indicate that an acceptable quantity has been provided to the patient, then no further action may be necessary. However, if the query determines that the patient has been provided with either insufficient or excess quantity of the pharmaceutical, then an alarm notification may be generated and provided to the patient and/or to the medical practitioner though the notification system 14. An alarm notification to the patient, or responsible party, may include a request that the patient contact the doctor for further advice and consultation, a reminder to take their prescribed medication, a warning against taking too much of the prescribed medication, or any suitable notification. In addition to providing the alarm notification, the system may register that the patient is to be monitored more closely and thus schedules the query to be executed with greater frequency.

The prompting of the data query may be controlled from the practice management system, for example, through some suitable reminder tracking system, or may be controlled from within the management network, for example, through regular scheduling. In one embodiment, the management network may be configured to periodically download filters, for example, daily, weekly, etc, from the different practice management systems 12a, 12b and execute queries based on those filters either at the time of download or at some other time, for example as per a query schedule downloaded with the filters.

Figure 5:
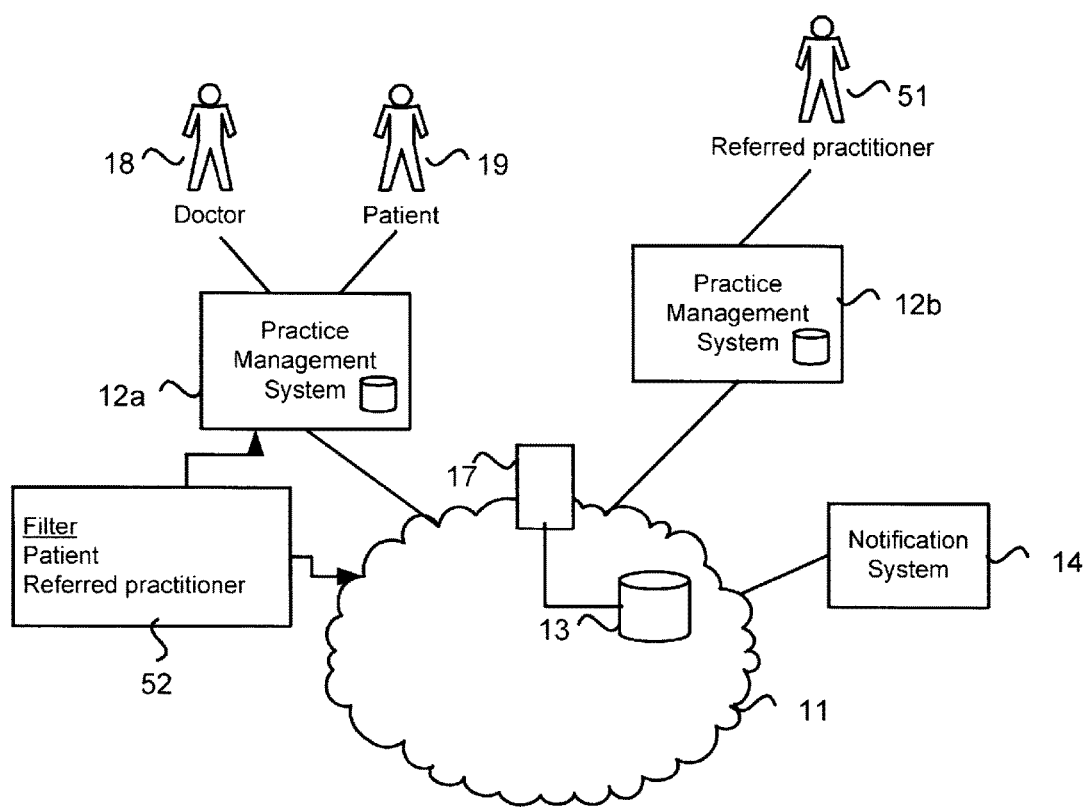
FIG. 5 schematically represents an embodiment of the disclosure relating to monitoring provision of referred services.

In one embodiment, illustrated in FIG. 5, the management network 11 can execute a query on a therapy parameter of a patient's treatment regime. For example, a medical practitioner 18 at the practice managed by practice management system 12a may prescribe to a patient a physiotherapy, chiropractic, psychological, specialist or other similar treatment. The prescribed treatment may be offered, for example, through a distinct or separate practice, such as the medical practice managed by practice management system 12b. The additional therapy may be a single consultation or may be a course of consultations or treatments with a referred practitioner 51. When the additional treatment is prescribed, a filter 52 is generated and stored in the practice management system 12a and/or the management network 11. When a query based on the filter executes, the management network 11 interfaces with the practice management system 12b to determine if the patient has visited the practice managed by the practice management system 12b and the regularity of visits. As for the previously discussed example, alarm notifications can be generated to the patient and/or the prescribing practitioner 18 if the requirements of the prescribed treatment regime are not being met. The alarm notifications can be sent using the notification system 14. In addition, a notification may be sent to the practice management system 12b and/or a respective medical practitioner 51 allowing the practitioner 51 to actively pursue an appointment with the patient 19 in accordance with the prescribed treatment regime.

When prescribing a therapy parameter, a medical practitioner may provide a referral to a specific practitioner at a specific medical practice. Alternatively, the prescribing practitioner may specify that a therapy is required from any one of a class of therapists. For example, physiotherapy may be provided by any suitable physiotherapist at any suitable practice. In the present example, a query may execute on all medical practices within the system 10 to determine those practices that provide physiotherapy and then determine whether any of the physiotherapists have provided treatment to the patient. An action taken on the query results may be dependent on all visits to all physiotherapists or selected visits.

Figure 6:
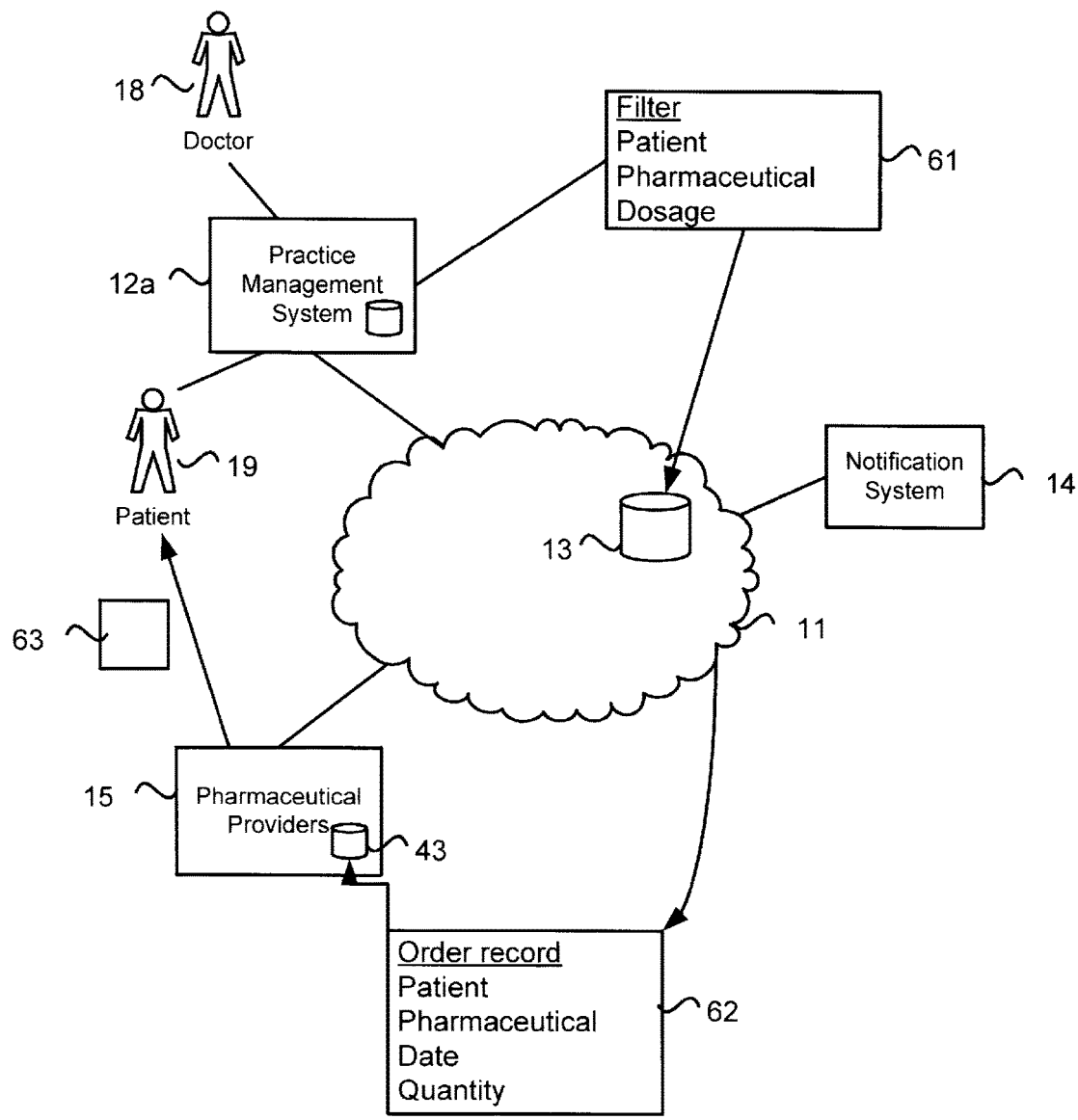
FIG. 6 schematically represents an embodiment of the disclosure relating to automatic provision of pharmaceuticals.

The system 10 provides an additional opportunity for automating the provision of a prescribed treatment regime. In an embodiment described with reference to FIG. 6, a prescribed treatment regime may include a regular and ongoing course of medication for a patient. A filter 61 may associate the patient with the prescribed medication and the dosage. From this data, a query may determine that a delivery of medication is required at a regular period, such as weekly, monthly, etc. When the query executes on the management network 11, the network 11 is able to provide an order notification 62 to the pharmaceutical network 15. From the notification, the pharmaceutical network is able to package and deliver a prescribed course of medication 63 to a patient delivery address detailed in the notification. Automating the delivery of various parameters of a prescribed treatment regime can provide advantage for house bound patients and their carers, by removing the requirement to leave the home to replenish stocks of medicines.

In one embodiment, the supply of services to patients in accordance with a prescribed treatment regime can also be automated. For example, a prescribed treatment may include regular physiotherapy, chiropractic, psychological, specialist or other similar treatment that might be offered, for example, through a distinct or separate practice, such as the medical practice managed by practice management system 12b. A filter associating the patient with the treatment may be executed on the management network to analyze an appointment schedule of the practice management system 12b. The query may determine an available appointment for the patient based on appointment scheduling preferences specified by the patient in the database 13, such as the patient's availability. When a suitable vacancy is found, the query automatically schedules the appointment and provides the patient with a notification detailing the appointment through the notification system 14. Automatically scheduling appointments may also include automatically scheduling of home visits by a medical practitioner, thereby aided in the care of house bound patients.

An advantage of the present disclosure is in the monitoring of patients with specific conditions that require preventative medication. Conditions may include, without limitation, diabetes, hypertension, heart conditions and many psychological conditions such as depression, bipolar disorder, schizophrenia etc. Such patients may require seldom visits to their respective medical practitioners provided that they are taking their regular course of medication at the required dose. The above described system may include a query that determines all patients with a specific condition and the rate at which they are replenishing their medication. Patients that have not re-ordered for a period, such as a dosage period, may be sent a reminder notification that their medication is likely to be nearing its consumption. The dosage period will generally be the period for which a packaged dosage of the medication is intended to last. For example, if a course of medication requires the consumption of one tablet per day and there are 14 tablets in a packaged dose, then a reminder notification may be provided to the patient if the query determines that no order has been made by the patient after, say, 12 days. If the query determines that no order has been placed by the patient for a period longer than the dosage period, then a more urgent warning notification may be provided to the patient and/or the prescribing practitioner.

The embodiments described herein are not to be limited to monitoring and/or automating patient care by practitioners only. In one embodiment, instead of the filters being provided from the practice management systems, a filter may be provided by a third party, such as a government organization. For example, a government organization 16 may be interested in determining all patients across all practice management systems with a particular condition. In a further example, a medical body may design a filter to determine all patients for whom a particular pharmaceutical has been prescribed in order to determine whether practitioners are prescribing pharmaceuticals correctly.

Although embodiments of the present invention have been illustrated in the accompanied drawings and described in the foregoing description, it will be understood that the invention is not limited to the embodiments disclosed, but is capable of numerous rearrangements, modifications, and substitutions without departing from the spirit of the invention as set forth and defined by the following claims. For example, the capabilities of the invention can be performed fully and/or partially by one or more of the blocks, modules, processors or memories. Also, these capabilities may be performed in the current manner or in a distributed manner and on, or via, any device able to provide and/or receive information. Further, although depicted in a particular manner, various modules or blocks may be repositioned without departing from the scope of the current invention. Still further, although depicted in a particular manner, a greater or lesser number of modules and connections can be utilized with the present invention in order to accomplish the present invention, to provide additional known features to the present invention, and/or to make the present invention more efficient. Also, the information sent between various modules can be sent between the modules via at least one of a data network, the Internet, an Internet Protocol network, a wireless source, and a wired source and via plurality of protocols.

The invention claimed is:

1. A computer-readable medium containing an instruction that when executed by a processor causes the processor to perform:
   receiving, into a first patient management system of a first medical practice coupled to a management network that is associated with a plurality of separate practice management systems, and via a user interface, a patient treatment regime prescribed to a patient by the first medical practice, the patient treatment regime including a prescription for a pharmaceutical to the patient;
   determining, by the first patient management system, a query dependent on the at least one patient treatment regime, the query comprising a filter that specifies an acceptable limit for consumption of the pharmaceutical associated with the patient;
   automatically executing, by the first patient management system, the query, in accordance with a query schedule, to determine whether the patient is conforming to the patient treatment regime by reference to data within the first patient management system or a second patient management system and without requiring human input to execute the query, wherein the second patient management system comprises a pharmaceutical network;
   receiving, by the first patient management system, and from the pharmaceutical network, a query result indicating whether a quantity of the pharmaceutical provided to the patient conforms to the acceptable limit for consumption;
   executing, by the first patient management system, at least one action dependent on whether the patient is conforming to the patient treatment regime, wherein the at least one action comprises:
      automatically modifying the query schedule to increase a frequency at which the query is executed based on the patient not conforming with the patient treatment regime and to decrease a frequency at which the query is executed, based on the patient conforming with the patient treatment regime, and
      providing, by the first patient management system, an alarm notification using a notification system when the query result indicates that the quantity of the pharmaceutical provided to the patient does not conform to the acceptable limit for consumption and providing the alarm notification to at least one of the patient and a medical practitioner through the notification system, and
   wherein the at least one action further comprises automatically scheduling an appointment for the patient by referencing a patient availability and notifying the patient of the scheduled appointment through the notification system.

2. The computer-readable medium according to claim 1, wherein the at least one action further comprises:
   generating a notification and providing said generated notification to said first medical practice.

3. The computer-readable medium according to claim 1, wherein the at least one action comprises:
   generating a notification and providing said generated notification to at least one of said patient and a responsible party associated with said patient.

4. The computer-readable medium according to claim 1, comprising:
   determining whether the patient has received the at least one therapy.

5. A method of automating a patient treatment regime, the method comprising:
   prescribing, by a first patient management system of a first medical practice, the patient treatment regime, the patient treatment regime including a prescription for a pharmaceutical to the patient;
   storing, by a first patient management system, at least one parameter of the patient treatment regime in a database of the first patient management system, the first patient management system being coupled to a management network that is associated with a plurality of separate patient management systems;
   creating, by a first patient management system, a filter associating the patient with the patient treatment regime, the filter specifying an acceptable limit for consumption of the pharmaceutical by the patient;
   automatically executing, by the first patient management system, a query, in accordance with a query schedule, to determine if the patient is conforming to the patient treatment regime by reference to data within the first patient management system or a second patient management system and without requiring human input to execute the filter, wherein the second patient management system comprises a pharmaceutical network;
   receiving, by the first patient management system, and from the pharmaceutical network, a query result indicating whether a quantity of the pharmaceutical provided to the patient conforms to the acceptable limit for consumption;

executing, by the first patient management system, at least one action that is dependent on whether the patient is conforming to the patient treatment regime, wherein said at least one action comprises:

automatically modifying the query schedule to increase a frequency at which the query is executed based on the patient not conforming with the patient treatment regime and to decrease a frequency at which the query is executed, based on the patient conforming with the patient treatment regime, and providing, by the first patient management system, an alarm notification using the notification system when the query result indicates that the quantity of the pharmaceutical provided to the patient does not conform to the acceptable limit for consumption and providing the alarm notification to at least one of the patient and a medical practitioner through the notification system, and wherein the at least one action further comprises automatically scheduling an appointment for the patient by referencing a patient availability and notifying the patient of the scheduled appointment through the notification system.

6. The method according to claim 5, further comprising:
determining a supplier of the pharmaceutical; and
generating a delivery of the pharmaceutical to the patient.

7. The method according to claim 5, further comprising:
scheduling at least one appointment between the patient and the at least one practitioner.

8. The method according to claim 7, further comprising:
generating a notification of the appointment and providing the generated notification to the patient.

9. The method according to claim 7, further comprising:
accessing a practice management system associated with the at least one practitioner to schedule the at least one appointment.

10. A system for providing a treatment regime to a patient, the system comprising:

at least one database storing one or more patient preferences;

at least one notification system communicably coupled to the at least one database;

at least one processor of a first patient management system communicably coupled to the at least one database and to a management network that is associated with a plurality of separate patient management systems, the management network comprising at least one data source external to the at least one database, wherein the at least one processor is to:

receive a patient treatment regime prescribed to a patient by a first medical practice associated with the first patient management system, the patient treatment regime including a prescription for a pharmaceutical to the patient;

determine a query dependent on the at least one patient treatment regime, the query comprising a filter that specifies an acceptable limit for consumption of the pharmaceutical associated with the patient;

automatically execute, in accordance with a query schedule, the query to determine whether the patient is conforming to the patient treatment regime by reference to data within the first patient management system or a second patient management system and without requiring human input to execute the query, wherein the second patient management system comprises a pharmaceutical network;

receive a query result from the pharmaceutical network indicating whether a quantity of the pharmaceutical provided to the patient conforms to the acceptable limit for consumption;

execute at least one action dependent on whether the patient is conforming to the patient treatment regime, wherein, when the at least one processor is to execute the at least one action, the at least one processor further is to:

automatically modify the query schedule to increase a frequency at which the query is executed based on the patient not conforming with the patient treatment regime and to decrease a frequency at which the query is executed, based on the patient conforming with the patient treatment regime, and provide an alarm notification using a notification system when the query result indicates that the quantity of the pharmaceutical provided to the patient does not conform to the acceptable limit for consumption and provide the alarm notification to at least one of the patient and a medical practitioner through the notification system, and wherein, when the at least one processor is to execute the at least one action, the at least one processor further is to:

automatically schedule an appointment for the patient by referencing a patient availability and notifying the patient of the scheduled appointment through the notification system.

11. The system according to claim 10, wherein the at least one processor further is to:
determine at least one notification preference of said patient from said database.

12. The system of claim 11, wherein the at least one notification system provides the notification to the patient in accordance with the at least one notification preference.

* * * * *